United States Patent [19]

Kinsman et al.

[11] 4,367,151

[45] Jan. 4, 1983

[54] METHOD OF TREATING TEXTILES WITH AMIDOAMINE OXIDES OF POLYMERIC FATTY ACIDS

[75] Inventors: Donald V. Kinsman, Fort Thomas, Ky.; Clement H. Luken, Jr., Cincinnati, Ohio

[73] Assignee: Emery Industries, Inc., Cincinnati, Ohio

[21] Appl. No.: 295,392

[22] Filed: Aug. 24, 1981

Related U.S. Application Data

[62] Division of Ser. No. 232,101, Feb. 16, 1981.

[51] Int. Cl.³ .......................................... D06M 13/40
[52] U.S. Cl. .................................... 252/8.8; 252/547; 260/407; 260/404.5
[58] Field of Search ............................ 427/389.9, 392; 260/404.5 PA, 404.5 R, 404.5 N, 407; 252/8.8 AM, 8.8 R, 547; 260/18 N; 8/137

[56] References Cited

U.S. PATENT DOCUMENTS

| | | | |
|---|---|---|---|
| 2,540,678 | 2/1951 | Kelley | 252/8.8 AM X |
| 3,086,943 | 4/1963 | Lang | 252/547 |
| 3,201,471 | 8/1965 | Fisher | 260/407 |
| 3,299,138 | 1/1967 | Sveum | 260/407 |
| 3,711,414 | 1/1973 | Hewitt | 252/8.8 R X |
| 3,755,559 | 8/1973 | Hewitt | 252/117 |
| 4,077,990 | 3/1978 | Prodo et al. | 260/404.5 R |

OTHER PUBLICATIONS

M. Weinstein and L. Smith, "Formulating with Amine Oxides", Household and Personal Products Industry, vol. 16, No. 1, Jan. 1979, pp. 74, 75 & 85.

*Primary Examiner*—Thurman K. Page
*Attorney, Agent, or Firm*—Kenneth D. Tremain

[57] ABSTRACT

Highly useful amidoamine oxides are provided which are derived from polymeric fatty acids, particularly, dimer and trimer acids obtained by the polymerization of $C_{18}$ unsaturated monocarboxylic acids. Aqueous solutions and dispersions of the amidoamine oxides of this invention can be used in a variety of formulations to impart desirable properties. They are particularly advantageous for use in cleaning formulations and shampoo products and when included in anionic and cationic laundry detergents have been found to soften the laundered articles.

6 Claims, No Drawings

METHOD OF TREATING TEXTILES WITH AMIDOAMINE OXIDES OF POLYMERIC FATTY ACIDS

This is a division of application Ser. No. 232,101, filed Feb. 16, 1981.

BACKGROUND OF THE INVENTION

1. Field of the Invention:

This invention relates to novel amidoamine oxides of polymeric fatty acids and, more particularly, to amidoamine oxides of $C_{36}$ dicarboxylic acids useful as fabric softening agents. The invention also relates to a method of softening fibers, yarns and fabrics by treating with the novel amidoamine oxides.

2. Description of the Prior Art:

Amine oxides and diamine dioxides are known and have been widely utilized in detergent compositions. For example British Pat. No. 1,234,591 discloses a detergent composition for washing fabrics comprised of a sulphoxy detergent, a water-soluble builder and an amine oxide of the formula

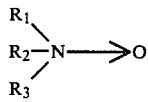

where $R_1$ is an alkyl or alkenyl radical, and $R_2$ and $R_3$ are alkyl or hydroxyalkyl. Detergent compositions based on diamine dioxides are also disclosed in Belgium Pat. No. 626,346.

Amidoamine oxides based on monocarboxylic acids, such as propionic acid, lauric acid, myristic acid, palmitic acid, coconut fatty acids and the like are also known and commercially available. These amidoamine oxide products are typically employed in cleaning and shampoo formulations as foaming agents, wetting agents, thickeners and conditioners.

For a general discussion regarding the use of amine oxides and amidoamine oxides reference may be had to the article by M. Weinstein and L. Smith entitled "Formulating with Amine Oxides" (Household and Personal Products Industry, Vol. 16, No. 1, January 1979, p. 74).

U.S. Pat. No. 3,920,731 discloses amidoamine oxides derived from alkenyl succinic anhydrides which are useful in a wide variety of detergent formulations. The amidoamine oxides of U.S. Pat. No. 3,920,731 correspond to the formula

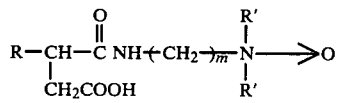

where R is an alkyl or alkenyl radical, R' is an alkyl group and m is an integer from 2 to 3.

U.S. Pat. No. 4,093,711 discloses dental preparations useful for retarding pellicle and plaque formation containing amidoamine oxides derived from mono- or dicarboxylic acids of the formula

where n is 1 or 2 and R is hydrocarbyl radical containing at least 13 carbon atoms and not more than 21 carbon atoms.

SUMMARY OF THE INVENTION

The present invention relates to amidoamine oxides derived from polymeric fatty acids and which correspond to the general formula

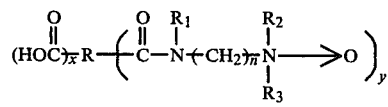

where $R_1$ is hydrogen or a $C_{1-4}$ alkyl group, $R_2$ and $R_3$ are $C_{1-4}$ alkyl groups, n is an integer from 2 to 5, R represents the hydrocarbon radical residue of the polymeric fatty acid, y is 1, 2 or 3 and x is an integer so that $x+y$ is equal to 2 or 3. Highly desirable products are derived from polymeric fatty acids obtained by the polymerization of unsaturated $C_{18}$ monocarboxylic acids and polymeric fatty acids containing 75% by weight or more $C_{36}$ dimer acids are particularly useful.

The amidoamine oxides are obtained by first reacting the polymeric fatty acid with a diamine containing a tertiary amine group and then oxidizing the amidoamine to the amidoamine oxide by treating with hydrogen peroxide or an organic peroxide or hydroperoxide. The products of this invention are obtained as aqueous solutions or dispersions containing 1 to 60 weight percent, and more generally 5 to 25 weight percent, solids.

The amidoamine oxides are highly useful softening and lubricating agents for use in textile applications. When applied to fibers, yarns and fabrics in an amount up to about 5 wt. percent, they impart highly desirable properties thereto. The polymeric fatty acid derived amidoamine oxides may be directly applied to fibers, filaments, yarns and fabrics from aqueous solutions or may be formulated with other ingredients. Detergent formulations containing these amidoamine oxides are particularly useful and fabrics washed with such detergent formulations exhibit improved softness.

DETAILED DESCRIPTION

The amidoamine oxides of this invention derived from polymeric fatty acids are obtained by first reacting the polymeric fatty acid with a diamine containing one tertiary amine group and thereafter converting the resulting amidoamine to the amidoamine oxide by oxidation with peroxide.

Polymeric fatty acids used for the preparation of these novel amidoamine compounds are obtained by the polymerization of olefinically unsaturated monocarboxylic acids containing from about 16 to 20 carbon atoms, such as oleic acid, linoleic acid and the like. The polymeric fatty acids are known as are processes for their production which typically include: treatment of unsaturated fatty acids with acid catalysts such as HF, $BF_3$, and the like; thermal polymerization of unsaturated fatty acids conducted in the presence or absence of treated or untreated clay catalysts; and treatment of unsaturated fatty acids with peroxides. By way of illustration of the preparation of polymeric fatty acids, reference may be had to U.S. Pat. Nos. 2,793,219 and 2,955,121.

Polymeric fatty acids obtained from the polymerization of unsaturated fatty acids are primarily comprised of dimer and trimer acids; however, there may also be present in the mixture some higher acids and unreacted monomer. For the preparation of the amidoamines of this invention polymeric fatty acids containing from 97 to 10 weight percent dimer and 3 to 90 weight percent trimer are employed.

Particularly useful polymeric fatty acids are obtained by the polymerization of $C_{18}$ unsaturated monocarboxylic acids, such as oleic acid and linoleic acid or mixtures thereof (e.g. tall oil fatty acids). These polymeric fatty acid products have as their principal components $C_{36}$ dimer and $C_{54}$ trimer acids. Superior results are obtained with acids of this type which contain 75% by weight or more and $C_{36}$ dimer acid, the remainder of the product consisting essentially of $C_{54}$ trimer. High dimer content polymeric fatty acids containing substantially reduced amounts of higher polymer acids and unreacted unsaturated monocarboxylic acid can be obtained by molecular distillation or by the use of other highly efficient distillation procedures. The polymeric fatty acid may also be hydrogenated prior to use.

Diamines reacted with the polymeric fatty acid contain a tertiary amine group. The remaining amine function can be either a primary or secondary amine. Useful diamines of this type correspond to the general formula

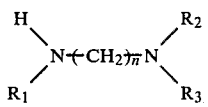

wherein $R_1$ is a hydrogen or a $C_{1-4}$ alkyl group, $R_2$ and $R_3$ are $C_{1-4}$ alkyl groups and n is an integer from 2 to 5, preferably 2 or 3. Especially useful diamines for the preparation of the amidoamines of this invention include dimethylaminopropylamine, diethylaminopropylamine, dimethylaminoethylamine and diethylaminoethylamine.

The diamine and polymeric fatty acid are reacted by heating the reactants at an elevated temperature, generally between about 105° C. and 200° C., and removing the water formed during the reaction. The reaction can be monitored by measuring the amount of water recovered. It is not necessary that all of the carboxyl groups be reacted and useful amidoamines are obtained when only one of the available carboxyl groups of the polymeric fatty acid is reacted. Thus, in the case of dimer, 0.5 to 1.0 equivalent primary or secondary amine can be reacted per carboxyl equivalent and, in the case of trimer, 0.33 to 1.0 equivalent primary or secondary amine can be reacted per carboxyl equivalent. When all of the carboxylic functionality of the polymeric fatty acid is to be reacted, an excess of amine can be employed to facilitate the reaction.

The reaction of the polymeric fatty acid and diamine can be carried out in the absence of a solvent; however, it is sometimes advantageous to utilize an inert hydrocarbon diluent as the reaction medium. Particularly useful solvents for the reaction are aromatic hydrocarbons, such as toluene, xylene, and the like, which form an azeotrope with water. By the use of such solvents removal of water of reaction from the reaction mixture is facilitated. Catalysts need not be employed to bring about reaction of the carboxyl and amine; however, conventional amidation catalysts can be utilized if desired.

The resulting polymeric fatty acid amidoamine is then converted to the amidoamine oxide by reacting with an oxidizing agent, such as hydrogen peroxide, in accordance with conventional methods known to the art. Whereas hydrogen peroxide is the most widely used oxidant for the preparation of amine oxides, other organic peroxides and organic hydroperoxides can also be used. The reaction generally involves simply heating the amidoamine with a molar excess, most usually 10 to 30%, of the peroxide.

The compositions of the resulting amidoamine oxides can vary considerably depending on the particular polymeric fatty acid employed, i.e. the dimer/trimer content, and the amount of diamine reacted with the polymeric fatty acid. In general, however, the amidoamine oxides of this invention will correspond to the formula

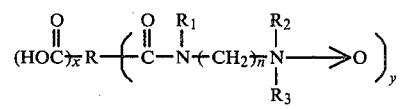

where $R_1$, $R_2$, $R_3$ and n are the same as defined above for the diamine, R represents the hydrocarbon radical residue of the polymeric fatty acid, and, y is 1, 2 or 3 and x is an integer so that $x+y$ is equal to 2 or 3.

The amidoamine oxides of this invention derived from polymeric fatty acids are obtained as aqueous solutions or dispersions which can range from highly viscous gel-like masses to readily pourable fluids and will typically contain from 1 to 60 percent, by weight, solids. More usually, the aqueous solutions or dispersions contain 5 to 25 percent by weight solids, i.e. amidoamine oxide product.

The amidoamine oxides can be employed in numerous formulations adaptable for use in a wide variety of applications. They are compatible with anionic and nonionic detergents and can be utilized in bath and shampoo formulations, industrial and household cleaning formulations, wash formulations and the like. In addition to imparting the usual properties generally associated with the use of conventional amidoamine oxides, the products of this invention based on polymeric fatty acids impart other desirable features as a result of their unique chemical, physical and structural properties. For example, it has been observed that some household cleaning formulations prepared using the amidoamine oxides of this invention exhibit reduced skin irritation. The amidoamine oxides of this invention also exhibit superior thickening characteristics with various liquid formulations in which they are used. Thick shampoos having good foaming characteristics and exhibiting low irritability are produced using these products. It has further been noted that hair washed with shampoos formulated with the polymeric fatty acid amidoamine oxides has improved wet-comb properties.

These polymeric fatty acid derived amidoamine oxides are highly useful softening and lubricating agents for fibers, filaments, yarns, fabrics and the like. They can be used in industrial applications but also have household utility. They are applied to fibers, yarns and fabrics in an amount up to 5 percent, by weight. Application can be made directly from solution, as is generally the case in industrial applications where softeners are padded or rolled onto the material being treated or the material is immersed in or passed through a bath containing the amidoamine oxide. The amidoamine oxides may also be formulated with other known treating agents and applied therewith. Detergent formulations containing the products of this invention are particularly useful and fabrics washed with such detergents exhibit improved softness so that in many instances the addition of fabric softener in the rinse cycle can be completely eliminated.

Depending on the particular formulation and application intended, the amidoamine oxides are employed at levels from 0.5 up to about 20 wt. percent of the total formulation. More usually they are present from about 1 to 10 wt. percent. The products of this invention are compatible with most conventional formulating ingredients and special processing is not required for the preparation of formulations containing these products.

The following examples illustrate the invention more fully. In these examples parts and percentages are given on a weight basis unless otherwise indicated.

EXAMPLE I

An amidoamine oxide of a polymeric fatty acid was prepared as follows: To a glass reactor were charged 368.6 gms polymeric fatty acid (Empol ® 1010 Dimer Acid - 97% $C_{36}$ dimer acid; 3% $C_{54}$ trimer acid; acid value 198) and 30 mls xylene. The mixture was heated to 200° C. with stirring while nitrogen gas was introduced subsurface at a rate of 0.5 SCFH. Dimethylaminopropylamine (159.5 gms; 20% excess based on available carboxyl functionality) was then added dropwise over a period of 2.5 hours while maintaining the temperature at 200° C. When the addition was complete, heating was continued for an additional 4 hours at which time the acid value of 0.84. During the addition and subsequent heating water was removed from the reaction mixture via a water trap attached to a condenser. The temperature was then reduced, a vacuum applied and xylene distilled from the reaction mixture. The product, consisting primarily of bis-(3-N,N-dimethylaminopropane-1)-dimer diamide, was recovered as a heavy viscous oil.

To convert the resulting diamidoamine product to the diamidoamine oxide, 170 gms of the above-prepared product was dispersed in 1000 mls distilled water using a Premier Dispersator Unit and 56.7 gms 30% aqueous hydrogen peroxide added over a 15 minute period. The mixture was then treated at 70° C. while continuing dispersion. Heating was terminated after 3 hours, the reaction mixture cooled, and stored for future use. The resulting amber highly viscous liquid product contained 16 percent solids, predominantly dimer di-(1-amidopropane-3-N,N-dimethylamine oxide).

EXAMPLE II

Employing the procedure of Example I, an amidoamine oxide was prepared from a polymeric fatty acid containing 87% $C_{36}$ dimer acid and 13% trimer acid. For the reaction 352.2 gms of the polymeric fatty acid (Empol ® 1016) was combined with 30 mls xylene, heated to 200° C. under a nitrogen atmosphere and 147.2 gms (20% equivalents excess) dimethylaminopropylamine added over a 2 hour period. Heating was continued at 200° C. while removing water until the acid value was 2.3. The reaction was terminated at that point and the xylene removed by vacuum distillation. One-hundred and seventy grams of the resulting amidoamine product was then dispersed in water (1000 mls) and reacted with 30% hydrogen peroxide (55.5 gms). The amber liquid product (14.5% solids) was slightly less viscous than the product obtained in Example I, possibly due to the lower solids content. Similar results are obtained when a polymeric fatty acid containing 80% $C_{54}$ trimer acid and 20% $C_{36}$ dimer acid is employed.

EXAMPLE III

To demonstrate the ability to vary the compositions of this invention an experiment was conducted wherein only a portion of the available carboxylic functionality was reacted. The procedure for obtaining these products was generally the same as that described in Example I except for the fact that the amount of diamine employed was not sufficient to react with all of the available carboxyl functionality. For the reaction, 250 gms polymeric fatty acid (87% $C_{36}$ dimer, 13% $C_{54}$ trimer) and 104.73 gms dimethylaminopropylamine were reacted at 200° C. until an acid value of 46.8 was obtained. Based on this acid value, approximately 70% of the carboxylic groups were reacted and converted to the amidoamine. Upon removal of unreacted diamine and xylene from the reaction mixture, 170 gms of the "partial" amidoamine product was dispersed in 1000 mls water and reacted with 47.7 gms 30% hydrogen peroxide to obtain the amidoamine oxide. The final product, containing 18.6% solids, was a readily pourable amber fluid at room temperature.

EXAMPLE IV

To demonstrate the superior softening ability of the amidoamine oxide products of this invention derived from polymeric fatty acids, the products of Examples I and II were applied to stripped and desized cotton terry cloth. For the evaluation 2.5% aqueous solutions were prepared and uniformly applied to the cloth in an amount such that each cloth would absorb twice its own weight of the softener solution. The cloths were then allowed to air dry at room temperature and evaluated by a panel for softness. Duplicate samples of each cloth sample were ranked on a scale from 0 (very harsh) to 100 (very soft) by each panel member and the average rating obtained. Results were as follows:

|  | AVERAGE PANEL RATING |
| --- | --- |
| Product I | 80 |
| Product II | 80 |
| Untreated Control | 50 |

The softening effect of the dimer-based amidoamine oxides is evident from the above data. When an identical evaluation was conducted using an amidoamine oxide derived from a conventional short-chain dibasic acid (azelaic acid), an average panel rating of only 70 was obtained. In addition to being considerably softer, it was noted by the panel that the cloths treated with the products of this invention exhibited a much higher degree of lubrication than samples treated with the amidoamine oxide derived from azelaic acid.

EXAMPLE V

To demonstrate the ability to obtain softening at much reduced concentrations using the products of this invention, Example IV was repeated with the product of Example I. For this experiment, 1.5%, 1.0%, 0.5% and 0.25% aqueous solutions were prepared and applied to stripped and desized cotton terry cloth samples. Each cloth was allowed to absorb twice its own weight of solution. The dried cloths were then evaluated for softness and ratings were as follows:

|  | SOFTNESS RATING |
| --- | --- |
| Cloth containing 3.0% softener | 75 |
| Cloth containing 2.0% softener | 70 |
| Cloth containing 1.0% softener | 70 |
| Cloth containing 0.5% softener | 80 |
| Untreated control | 67 |

From the above results it is apparent that effective softening is obtained employing very low levels of the amidoamine oxides of this invention.

EXAMPLE VI

Anionic detergent formulations were prepared using the products of Examples II and III as follows:

|  | PERCENT |
| --- | --- |
| Linear alkylbenzene sulfonate | 25.0 |
| Sodium tripolyphosphate | 35.0 |
| Sodium silicate (wt. ratio $SiO_2/Na_2O$ = 2.0) | 15.0 |
| Coco Super dialkanolamide | 3.0 |
| Amidoamine oxide | 3.0 |
| Sodium sulfate | to 100 |

Stripped and desized cotton terry cloth were placed in Terg-O-Tometer pots with a wash solution (cloth:liquor ratio 1:20) containing 0.15% of the detergent formulation. The cloth samples were washed 10 minutes at 50° C. at 100 rpm and then followed with two 2 minute rinses at 50° C. and 100 rpm. After drying, the samples were evaluated for softness using the same rating procedure with the following results:

|  | AVERAGE PANEL RATING |
| --- | --- |
| Detergent containing product of Ex. II | 65.0 |
| Detergent containing product of Ex. III | 58.8 |
| Detergent containing Control* | 48.8 |

*Detergent formulation same as above except amidoamine oxide omitted.

Not only were the amidoamine oxides completely compatible with the anionic detergent formulation but, as evidenced by the data presented above, cloth treated with the detergent containing the amidoamine oxide was considerably softer than fabric washed with detergent not containing the product of this invention. Furthermore, the softness of the cloths treated with products II and III compared favorably to a control which was subsequently treated with a comparable amount of commercial laundry softener (Downy ®) in a separate rinse cycle.

EXAMPLE VII

An amidoamine oxide was prepared in the usual manner by reacting 344.5 gms polymeric fatty acid (87% $C_{36}$ dimer, 13% $C_{54}$ trimer) and 187.5 gms diethylaminopropylamine. Total reaction time at 200° C. was about 10 hours and the final acid value of the amidoamine product was 0.94. After removal of xylene, the amidoamine (170 gms) was dispersed in water and oxidized with 56.67 gms 30% hydrogen peroxide. The resulting clear yellow viscous solution of amidoamine oxide (24% solids) flowed readily at room temperature.

An anionic detergent formulation identical to that of Example VI was prepared using this product to evaluate the ability of the amidoamine oxide to impart softness during the wash cycle. The average panel rating obtained with the detergent formulation containing this product was 52.5 as compared to an average panel rating of 47.5 for cloth washed in the detergent formulation which did not contain the amidoamine oxide. Comparable results are obtained using an amidoamine oxide derived from a polymeric acid containing 75% $C_{36}$ dimer acid and 25% trimer acid (Empol ® 1024 Dimer Acid).

EXAMPLES VIII and IX

Nonionic liquid detergent formulations were prepared as follows:

|  | EX VIII (%) | EX IV (%) |
| --- | --- | --- |
| Nonylphenol polyethyleneglycol ether (10 POE) | 33.0 | 33.0 |
| Linear alkylbenzene sulfonate | 10.0 | 10.0 |
| Triethanolamine | 8.0 | 8.0 |
| Ethanol | 8.0 | 8.0 |
| Sodium silicate (wt. ratio $SiO_2/Na_2O$ = 2.4; Be.52.0°) | 5.0 | 5.0 |
| Amidoamine oxide of Example I | 2.0 | 5.0 |
| Water | to 100 | to 100 |

The detergents were evaluated as wash solutions following the procedure described in Example VI. Average panel softness ratings obtained for Examples VIII and IX were 53.3 and 52.5 respectively. A control washed with the same concentration of detergent containing no amidoamine oxide had an average panel rating of 47.

EXAMPLE X

To further demonstrate the versatility of the amidoamine oxide products of this invention and the superior results obtained therewith, the following liquid hair shampoo formulations were prepared:

|  | PERCENT | |
| --- | --- | --- |
|  | PRODUCT A | PRODUCT B |
| Mixed mono- and triisopropanolamine soaps of coconut and oleic fatty acids | 12.5 | 12.5 |
| Ethylenediaminetetraacetic acid —Na salt | 2.0 | 2.0 |
| $C_{14-16}$ alpha olefin sulfonate —Na salt | 2.0 | 2.0 |
| Amidoamine oxide of Example I | 3.0 | — |
| Amidoamine oxide of capric acid | — | 3.0 |
| Water | 80.0 | 80.0 |
| The shampoos had the following properties: |  |  |
| pH (1% solution; 27° C.) | 8.3 | 8.4 |
| Calcium resistance (PPM; 0.5% solution) | 74.0 | 74.0 |
| Ross-Miles Foam Test (1% solution; 27° C.) |  |  |
| t = 0 minutes | 14.3 cm | 15.2 cm |
| t = 5 minutes | 14.2 cm | 15.2 cm |
| Viscosity at 29° C. (cSt.) | 146.0 | 10.5 |

Both shampoo formulations were comparable in regard to their sudsing ability, however, product A formulated with the amidoamine oxide of this invention was substantially thicker and had a richer feel than product B prepared using the amidoamine oxide derived from the $C_{10}$ monocarboxylic acid. Furthermore, in tests conducted with standard virgin hair swatches, the hair washed with product A exhibited much improved wet combing characteristics compared to hair washed with Product B, i.e. the shampoo formulated with the amidoamine oxide of capric acid.

We claim:

1. A method of softening and lubricating filaments, fibers, yarns and fabrics which comprises applying thereto an effective amount of an amidoamine oxide of the formula

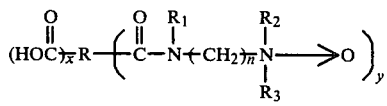

where R represents the hydrocarbon radical residue of a polymeric fatty acid obtained from the polymerization of $C_{16-18}$ unsaturated monocarboxylic acids, $R_1$ is hydrogen or an alkyl group having 1 to 4 carbon atoms, $R_2$ and $R_3$ are alkyl groups having 1 to 4 carbon atoms, n is an integer from 2 to 5, y is 1, 2 or 3 and x is an integer so that $x+y$ is equal to 2 or 3.

2. The method of claim 1 wherein the amidoamine oxide is applied from an aqueous solution or dispersion.

3. The method of claim 1 wherein the amidoamine oxide is applied from a detergent formulation.

4. The method of claims 1, 2 or 3 wherein the amidoamine oxide is derived from a polymeric fatty acid obtained from the polymerization of $C_{18}$ unsaturated monocarboxylic acids and contains from 97% to 10% by weight $C_{36}$ dimer and 3% to 90% by weight $C_{54}$ trimer.

5. The method of claim 4 wherein n is 2 or 3, $R_1$ is hydrogen, and $R_2$ and $R_3$ are methyl or ethyl groups.

6. The method of claim 5 wherein the polymeric fatty acid contains 75% by weight or more $C_{36}$ dimer acid.

* * * * *